United States Patent
Herlihy et al.

(10) Patent No.: US 7,612,122 B2
(45) Date of Patent: Nov. 3, 2009

(54) PIPERAZINO BASED PHOTOINITIATORS

(75) Inventors: Shaun Lawrence Herlihy, Chatham (GB); Brian Rowatt, Maidstone (GB); Robert Stephen Davidson, Leicester (GB)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 11/718,952

(22) PCT Filed: Nov. 9, 2005

(86) PCT No.: PCT/IB2005/004157

§ 371 (c)(1),
(2), (4) Date: Sep. 27, 2007

(87) PCT Pub. No.: WO2006/082477

PCT Pub. Date: Aug. 10, 2006

(65) Prior Publication Data

US 2008/0045620 A1   Feb. 21, 2008

(30) Foreign Application Priority Data

Nov. 10, 2005   (GB)   .................................... 0424831

(51) Int. Cl.
*C08F 2/46* (2006.01)
*C08F 2/50* (2006.01)

(52) U.S. Cl. ............................. 522/150; 522/39; 522/90; 522/96; 522/100; 522/104; 522/107; 522/151; 522/153; 522/173; 522/178; 522/181; 544/392; 544/395

(58) Field of Classification Search ................. 522/39, 522/90, 96, 104, 100, 107, 150, 151, 153, 522/173, 178, 181; 544/392, 395
See application file for complete search history.

(56) References Cited

U.S. PATENT DOCUMENTS

| | | | |
|---|---|---|---|
| 4,048,034 A * | 9/1977 | Martan | 522/39 |
| 4,582,862 A | 4/1986 | Berner et al. | |
| 4,992,547 A * | 2/1991 | Berner et al. | 544/162 |
| 5,531,817 A | 7/1996 | Shields | |
| 6,022,906 A | 2/2000 | Ohwa et al. | |
| 2007/0066700 A1* | 3/2007 | Herlihy et al. | 522/16 |

FOREIGN PATENT DOCUMENTS

| | | |
|---|---|---|
| EP | 0204575 A | 12/1986 |
| EP | 0337705 A | 10/1989 |
| EP | 0465039 A | 1/1992 |
| JP | 06200204 | 7/1994 |
| WO | WO9628305 | 9/1996 |
| WO | WO9731071 | 8/1997 |
| WO | 2005007637 A | 1/2005 |

* cited by examiner

*Primary Examiner*—Sanza L McClendon
(74) *Attorney, Agent, or Firm*—Kramer Levin Naftalis & Frankel LLP

(57) ABSTRACT

Compounds of formula (I): [where: the substituents $R^1$ are individually selected from $C_1$-$C_{10}$ alkyl groups and optionally substituted benzyl groups; the substituents $R^2$ are individually selected from alkyl groups or, together with the nitrogen atom to which they are attached, represent a nitrogen-containing heterocyclic group; Z is selected from $C_6$-$C_{10}$ arylene groups and groups of formula —$(CHR^3)_n$—, where $R^3$ is hydrogen, hydroxy or a $C_1$-$C_4$ alkyl group, and n is 0 to 6; Y is carbonyl or —CH2—; Q is a residue of a mono- or poly-hydroxy compound; and x is 1 to 6; and esters thereof] are useful as multi-functional photoinitiators for use in coating compositions to be cured by radiant energy.

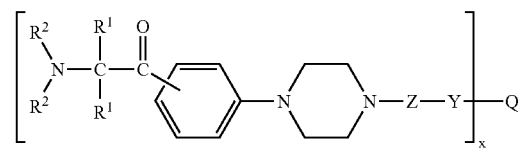

(I)

38 Claims, No Drawings

PIPERAZINO BASED PHOTOINITIATORS

CROSS REFERENCE TO RELATED APPLICATIONS

This application is the United States national stage filing of corresponding international application number PCT/IB2005/004 157 filed on Nov. 9, 2005 which claims priority to and benefit of Great Britain application number 0424831.6, filed Nov. 10, 2004, each of which is hereby incorporated herein by reference.

FIELD OF THE INVENTION

The present invention relates to a series of new piperazino compounds which are useful as photoinitiators, preferably multi-functional photoinitiators, for use in coating compositions to be cured by radiant energy, for example ultraviolet radiation. The invention also provides radiation-curable surface coating compositions, including varnishes, lacquers, printing inks and the like, which include at least one of the compounds of the present invention as a photoinitiator.

The compounds of the present invention comprise a polymeric core based on a polyhydroxy compound which is chemically bonded to one or more, preferably two or more, groups including a piperazino ring bonded to a benzene ring.

BACKGROUND OF THE INVENTON

Photoinitiators used in energy-curable surface coating formulations need to have good cure speed, and particularly good surface curing activity, low odour and good solubility. Moreover, as consumers become increasingly wary of extraneous compounds in foodstuffs, in order to comply with likely future legislation, the tendency of the compounds to migrate and be extracted should also be low. Furthermore, in order for the compounds to be useful in practice, it is necessary that they should be preparable with ease and economically on a commercial scale. It is becoming increasingly difficult to meet all of these requirements.

We have now discovered a series of piperazino compounds of the aminoalkylphenone photoinitiator class which have the potential to achieve low levels of photolysis product migration and low odour from the cured print. Their strong UV chromophores in the UVB region make the aminoalkylphenones particularly useful in pigmented printing inks.

Other compounds containing piperazino groups have been suggested for use as photoinitiators in U.S. Pat. Nos. 4,321, 118, 4,582,862, and EP 1357117. However, in these compounds, the piperazine ring is not attached directly to an aromatic ring, and the resulting compounds do not absorb UV radiation of the wavelengths used in commercial curing systems so efficiently.

GB 2320027 also discloses compounds similar to those of the present invention, but does not disclose compounds in which a piperazine ring is attached directly to an aromatic ring.

Thus, the present invention consists in a compound of formula (I):

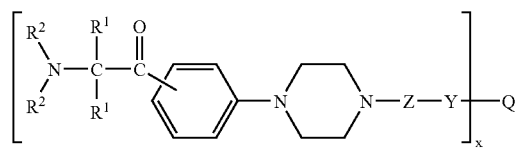
(I)

where:
the substituents $R^1$ are individually selected from $C_1$-$C_{10}$ alkyl groups and optionally substituted benzyl groups;
the substituents $R^2$ are individually selected from alkyl groups or, together with the nitrogen atom to which they are attached, represent a nitrogen-containing heterocyclic group;
Z is selected from $C_6$-$C_{10}$ arylene groups and groups of formula —$(CHR^3)_n$—, where $R^3$ is a hydrogen atom, a hydroxy group or a $C_1$-$C_4$ alkyl group, and n is a number from 0 to 6;
Y is selected from carbonyl groups and the —$CH_2$— group;
Q is selected from the residues of mono- or poly-hydroxy compounds having from 1 to 6 hydroxy groups; and
x is a number from 1 to 6;
and esters thereof.

SUMMARY OF THE INVENTION

The invention also provides an energy-curable composition comprising: (a) a polymerisable monomer, prepolymer or oligomer; (b) a compound of formula (I) or an ester thereof as photoinitiator, (c) optionally a pigment.

DETAILED DESCRIPTION OF THE INVENTION

The invention still further provides a process for preparing an energy cured polymeric composition by exposing this energy-curable composition to radiant energy, especially to ultraviolet radiation.

In the compounds of the present invention where $R^1$ represents an alkyl group, this may be a straight or branched chain alkyl group having from 1 to 10, preferably from 1 to 6, carbon atoms. Examples of such groups include the methyl, ethyl, propyl, isopropyl, butyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl, isohexyl, heptyl, octyl, nonyl and decyl groups, of which the methyl, ethyl, propyl, butyl and hexyl groups are preferred, the methyl and ethyl groups being most preferred.

Where $R^1$ represents a benzyl group, this may be substituted or unsubstituted, but is preferably unsubstituted. If the group is substituted, there is no restriction on the number of substituents, except that imposed by the number of substitutable positions and possibly by steric constraints, however, from 1 to 3 substituents would be common. Examples of such substituents include: alkyl groups, e.g. those having from 1 to 6 carbon atoms, such as the methyl, ethyl, propyl, isopropyl, butyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups; and alkoxy groups, e.g. those having from 1 to 6 carbon atoms, such as the methoxy, ethoxy, propoxy, butoxy, sec-butoxy, t-butoxy, pentyloxy and hexyloxy groups. However, the benzyl group is preferably unsubstituted.

Where $R^2$ represents an alkyl group, this may be a straight or branched chain alkyl group, preferably having from 1 to 6 carbon atoms, such as those exemplified above in relation to substituents on the benzyl group.

Alternatively, the two substituents $R^2$, together with the nitrogen atom to which they are attached, may represent a nitrogen-containing heterocyclic group. Such a group preferably has from 3 to 7 ring atoms, of which at least one, but preferably no more than 3, is a nitrogen atom. Of the remaining ring atoms, at least two are preferably carbon atoms, and one or more, preferably no more than one, are oxygen atoms. Examples of such heterocyclic groups include the morpholino, piperidino, 1-pyrrolidinyl, 3-alkyl-1-imidazolidinyl, 2-alkyl-1-pyrazolidinyl, 4-alkyl-1-piperazinyl, 1-pyrrolyl, 1-imidazolyl and 1-pyridyl groups, of which the piperidino, morpholino and 4-methyl-1-piperazinyl groups are preferred.

Where Z represents an arylene group, this may be a benzene ring, attached at the 1,2-, 1,3- or 1,4-positions, i.e. a phenylene group, or a naphthalene ring, attached at the 1,2-, 1,3-, 1,4-, 1,5-, 1,6-, 1,7- or 1,8-positions, preferably a benzene ring, attached at the 1,4-positions.

Where Z represents a group of formula —$(CHR^3)_n$—, and $R^3$ represents a $C_1$-$C_4$ alkyl group, the alkyl group may be a methyl, ethyl, propyl, isopropyl, butyl, isobutyl, sec-butyl or t-butyl group, preferably a methyl or ethyl group. Most preferably $R^3$ represents a hydrogen atom, or a methyl or ethyl group.

If n in the group of formula —$(CHR^3)_n$— is 0, then Z represents a direct bond. However, n is more preferably a number from 1 to 6, still more preferably from 1 to 3, and still more preferably 1 or 2 and most preferably 2.

An alternative preferred class of compounds of the present invention are those compounds of formula (I) where Z is a group of formula —$(CHR^3)_n$—, n is a number from 2 to 6 and one $R^3$ represents a hydrogen atom or a $C_1$-$C_4$ alkyl group, and the other or others of $R^3$ represent hydrogen atoms.

Y may be a carbonyl group or a —$CH_2$— group, preferably the carbonyl group.

In one embodiment of the present invention, Q represents a group of formula -$A_x$-Q', where A represents a group of formula —$[O(CHR^4CHR^5)_a]_y$—, —$[O(CH_2)_bCO]_y$— or —$[O(CH_2)_bCO]_{(y-1)}$—$[O(CHR^4CHR^5)_a]$—; and where:

$R^4$ and $R^5$ are the same or different and each represents a hydrogen atom or a $C_1$-$C_4$ alkyl group;

a is a number from 1 to 2;

b is a number from 4 to 5; and y is a number from 1 to 10;

x is a number from 1 to 6; and

Q' represents a residue of a mono- or poly-hydroxy compound having from 1 to 6 hydroxy groups.

In the compounds of this embodiment of the present invention, we prefer that A should represent a group of formula —$[O(CHR^4CHR^5)_a]_y$— where a is an integer from 1 to 2, y is as defined above, and $R^4$ and $R^5$ are the same or different and each represents a hydrogen atom or a $C_1$-$C_4$ alkyl group. More preferably A represents a group of formula —$[OCH_2CH_2]_y$—, —$[OCH_2CH_2CH_2CH_2]_y$— or —$[OCH(CH_3)CH_2]_y$—, where y is as defined above, or a group of formula —$[O(CH_2)_bCO]_y$— or —$[O(CH_2)_bCO]_{(y-1)}$—$[O(CHR^4CHR^5)_a]$—, where b is a number from 4 to 5 and $R^4$, $R^5$ and y are as defined above, y preferably being a number from 1 to 6.

In general, in the compounds of the present invention, y is preferably a number from 1 to 10, more preferably from 1 to 6. We also prefer compounds of this embodiment in which x is 2 and y is a number from 1 to 10.

The compounds of this embodiment of the present invention are preferably of a generally polymeric nature. The polymeric nature may be provided by either the group represented by Q' or the group represented by A or by both.

The polymeric polyhydroxy residue of formula -$A_x$-Q', which forms the core of the compounds of the present invention has a major influence on the behaviour of the compounds. In accordance with the present invention, it is preferred that it should have a polymeric nature, since the resulting compounds tend to be liquid or of low melting point, thus aiding dispersion in the coating composition. Compounds having a similar structure but not polymeric tend to be solid and/or insoluble in these coating compositions. However, we prefer that the core residue, of formula -$A_x$-Q', should not have too high a molecular weight, and prefer that the residue of formula -$A_x$-Q'should have a molecular weight no greater than 2000, preferably no greater than 1200, still more preferably no greater than 1000, and most preferably no greater than 800.

We particularly prefer that Q' is a residue of a $C_2$-$C_6$ alkylene glycol or of a polyalkylene glycol, in which the alkylene part has from 2 to 6 carbon atoms. More preferably, Q' is a residue of ethylene glycol, propylene glycol, butylene glycol, glycerol, 2,2-propanediol, polyethylene glycol, polypropylene glycol, polybutylene glycol, trimethylolpropane, di-trimethylolpropane, pentaerythritol or di-pentaerythritol.

It will be appreciated that, when the compounds of the present invention are analysed, the numbers a, b and y in the above formulae need not be integral, and, indeed, it is unlikely that they will be integral, since the compounds of the present invention may be mixtures of several compounds in which the numbers a, b and y differ. In accordance with the present invention, provided that the average value of each of these numbers is as defined above, this will be satisfactory. Of course, for each individual molecule of the compounds of the present invention, a, b and y will be integral, and it might be possible to separate out such individual compounds, but, in practice, mixtures of these compounds are used.

In another preferred embodiment of the present invention, x is 1. In this case, Q is preferably the residue of a compound of formula $R^6$—OH, where $R^6$ represents a $C_1$-$C_{10}$ alkyl group or an optionally substituted benzyl group, as exemplified above in relation to $R^1$. More preferably, Q is a $C_1$-$C_6$ alkoxy group or a phenoxy group. We also particularly prefer, in this embodiment, that Z is a phenylene group.

However, the compounds of the present invention are preferably multi-functional photoinitiators, and so x is preferably greater than 1, i.e. preferably from 2 to 6.

Thus, in an alternative preferred embodiment of the present invention, Q is a residue of a $C_2$-$C_6$ polyalkylene glycol, in which the alkylene part has from 2 to 6 carbon atoms. Alternatively, Q may be a bis($C_1$-$C_6$ hydroxyalkyl)ether, where the two hydroxyalkyl parts may be the same as or different from each other, although they are preferably the same, and each may have one or more hydroxy groups. In this embodiment, Q is preferably a residue of ethylene glycol, propylene glycol, butylene glycol, glycerol, 2,2-propanediol, polyethylene glycol, polypropylene glycol, polybutylene glycol, trimethylolpropane, di-trimethylolpropane, pentaerythritol or di-pentaerythritol.

The compounds of the present invention may be prepared simply, for example by a Michael addition of a compound of formula (II):

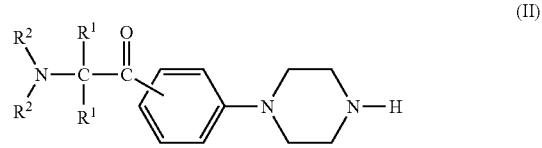

(II)

(in which $R^1$ and $R^2$ are as defined above) with an active compound corresponding to the group of formula —$(Z$—$Y)_x$-Q (where Z, Y, x and Q are as defined above). This active compound may, for example, be a compound including a carbon-carbon double bond or an epoxide group, as illustrated in more detail in the Examples appearing hereafter, and is preferably an acrylate or methacrylate.

The composition of the present invention may be formulated as a printing ink, varnish, adhesive or any other coating composition which is intended to be cured by irradiation, whether by ultraviolet or electron beam. Such compositions will normally contain at least a polymerisable monomer, prepolymer or oligomer, the photoinitiator of the present invention, an amine synergist and optionally a sensitiser, but may also include other components well known to those skilled in the art, for example, waxes, flow aids and, in the case of printing inks, a pigment.

A wide variety of monomers and prepolymers may be subjected to photoinitiation with the photoinitiators of the present invention, and the nature of the monomers and prepolymers is not critical to the present invention.

The radiation-curable monomer or oligomer is preferably an ethylenically unsaturated compound, for example an acrylate or methacrylate. Examples of suitable acrylate oligomers include aliphatic or aromatic urethane acrylates, polyether acrylates, polyester acrylates and epoxy acrylates (such as bisphenol A epoxy acrylate). Examples of suitable acrylate monomers include hexanediol diacrylate, trimethylolpropane triacrylate, di-trimethylolpropane tetraacrylate, di-pentaerythritol pentaacrylate, polyether acrylates, such as ethoxylated trimethylol propane triacrylate, glycerol propoxylate triacrylate, ethoxylated pentaerythritol tetraacrylate, epoxy acrylates such as dianol diacrylate (=the diacrylate of 2,2-bis[4-(2-hydroxyethoxy)phenyl]propane, Ebecryl 150 from UCB), glycol diacrylates such as tripropylene glycol diacrylates and alkyl acrylates and methacrylates (such as hexanediol diacrylate, isobornyl acrylate, octadecyl acrylate, lauryl acrylate, stearyl acrylate and isodecyl acrylate, and the corresponding methacrylates).

Also, the compositions of the present invention preferably contain a synergist, such as an aminoacrylate or a dimethylaminobenzoic acid ester, as is well known in the art. Preferably the synergist will be a dimethylaminobenzoic acid ester in the case of a printing ink or an aminoacrylate in the case of a varnish. Some inks, such as those used in flexographic printing applications, may contain both amine types.

If desired, in addition to the photoinitiator compound of the present invention, an additional photoinitiator may be employed, as is well known in the art. Examples of such additional photoinitiators which may be used in the compositions of the present invention include thioxanthones (and derivatives), benzophenones (and derivatives), hydroxyalkylphenones, xanthones and anthraquinones.

The amounts of the radiation-curable monomer or oligomer, photoinitiator, synergist, sensitiser and optional colorant will vary according to the type of varnish or ink, the particular equipment to be used to apply it and the application. However, typically, the amount of photoinitiator plus amine synergist is from 1% to 15-20% by weight of the total composition.

The compounds of formula (I) are especially suited for use in varnishes and inks, especially printing inks, including lithographic inks. These typically comprise, as additional components to those referred to above, one or more of pigments, waxes, stabilisers, and flow aids, for example as described in "Printing Ink Manual", fourth edition, Leach R. H. et al. (eds.), Van Nostrand Reinhold, Wokingham, (1988), the disclosure of which is incorporated herein by reference. In particular, the compounds are useful as photoinitiators in printing ink compositions, and so these compositions most preferably include at least one pigment.

Additives which may be used in conjunction with the principal components of the coating formulations of the present invention include stabilisers, plasticisers, pigments, waxes, slip aids, levelling aids, adhesion promoters, surfactants and fillers. Also other photoinitiators, such as thioxanthone (and derivatives), benzophenone (and derivatives), hydroxyalkylphenones, aminoalkylphenones and anthraquinone (and derivatives) may be included, if desired.

The compounds of the present invention may be included as photoinitiators in coating formulations such are well known in the art, and the precise composition of such formulations will vary depending upon the other components and the intended use, as is well known. However, a typical formulation for an ink coatable by flexography might be:

| | |
|---|---|
| Pigment | 8-20% |
| Photoinitiator + synergist | 4-10% |
| Monomer/prepolymer/oligomers | 30-90% |
| Additives | 0-10% | although inks may have compositions outside these ranges as is well known in the art.

The invention is further illustrated by the following non-limiting Examples.

EXAMPLE 1

Preparation of 2-benzyl-2-N,N-dimethylamino-1-[4-piperazinophenyl]-1-butanone

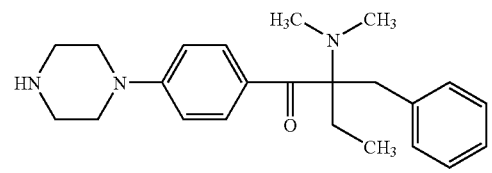

5.0 g of 2-benzyl-2-N,N-dimethylamino-1-[4-fluorophenyl]-1-butanone (0.0167 moles), 5.75 g of piperazine (0.0669 moles), 0.063 g of copper (I) iodide and 15 ml of toluene were mixed in a three necked flask equipped with a stirrer, nitrogen inlet, condenser, nitrogen outlet and a temperature probe. The mixture was heated to reflux for a total of 24 hours under a constant flow of nitrogen gas. The mixture was then cooled to room temperature, after which it was dissolved in 50 ml of dichloromethane. The mixture was then extracted with 100 ml of a saturated aqueous sodium chloride solution and then with 2×100 ml of water. The dichloromethane layer was then dried using anhydrous magnesium sulphate. The magnesium sulphate was removed by filtration and the organic solvent was then removed on a rotary evaporator to yield the product.

Product yield 5.50 g (90.23%) of a yellow solid.

The product was analysed by FT-IR and LCMS.

IR: Aryl C—N 1340 $cm^{-1}$,

MS: m/z $[M+1]^+$=366 (Mw=365).

EXAMPLE 2

Preparation of 2-methyl-1-[4-piperazinophenyl]-2-morpholino propan-1-one

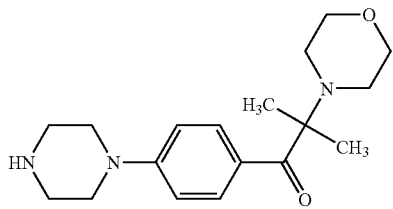

4.2 g of 2-methyl-1-[4-fluorophenyl]-2-morpholinopropan-1-one (0.0167 moles), 5.75 g of piperazine (0.0669 moles), 0.063 g of copper (I) iodide and 15 ml of toluene were mixed in a three necked flask equipped with a stirrer, nitrogen inlet, condenser, nitrogen outlet and a temperature probe. The mixture was heated to reflux for a total of 24 hours under a constant flow of nitrogen gas. The mixture was then cooled to room temperature, after which it was dissolved in 75 ml of dichloromethane. The mixture was then extracted with 100 ml of a saturated aqueous sodium chloride solution and then with 2×100 ml of water. The dichloromethane layer was then dried using anhydrous magnesium sulphate. The magnesium sulphate was removed by filtration and the organic solvent was then removed on a rotary evaporator to yield the product.

Product yield 4.52 g (85.4%) of a yellow solid.

The product was analysed by FT-IR and LCMS.

IR: Aryl C—N 1359 cm$^{-1}$.

MS: m/z [M+1]$^+$=318 (Mw=317).

EXAMPLE 3

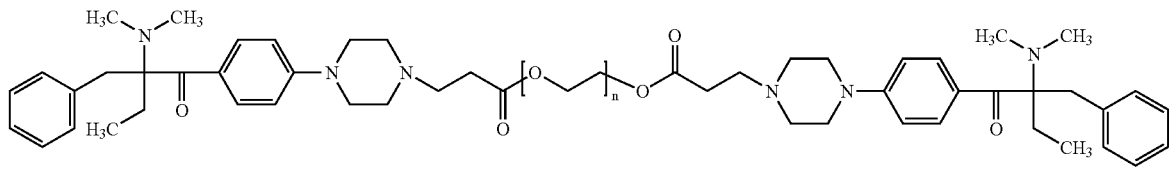

0.53 g PEG200 diacrylate (mol. wt. ~258, n=3 average) (0.00205 moles), 1.5 g of the product of Example 1 (0.00411 moles), toluene 10 ml and 0.05 g 1,8-diazabicyclo-(5.4.0) undec-7-ene (DBU) (catalyst) were mixed in a round bottomed flask equipped with a stirrer, condenser and temperature probe. The mixture was heated to reflux for a total of 6 hours. The mixture was then cooled and filtered, and then the solvent was removed on the rotary evaporator to yield the product.

Product yield 2.1 g of a viscous yellow/orange paste.

The product was analysed by FT-IR and LCMS.

IR: acrylate C=C at 810 cm$^{-1}$ not present, indicating product has formed.

MS: m/z [M+1]$^+$=989 (Mw=988 difunctional product); m/z [M+1]$^+$=624 (Mw=623 monofunctional fragment).

EXAMPLE 4

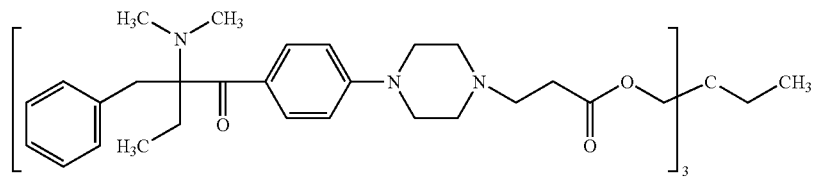

0.4055 g trimethylol propane triacrylate (TMPTA, mol. wt. 296) (0.00137 moles), 1.5 g of the product of Example 1 (0.00411 moles), toluene 10 ml and 0.05 g 1,8-diazabicyclo (5.4.0)undec-7-ene (DBU) (catalyst) were mixed in a round bottomed flask equipped with a stirrer, condenser and temperature probe. The mixture was heated to reflux for a total of 6 hours. The mixture was then cooled and filtered, and then the solvent was removed on the rotary evaporator to yield the product.

Product yield 2.00 g of a viscous yellow/orange paste.

IR: acrylate C=C at 810 cm$^{-1}$ not present, indicating product has formed.

MS: m/z [M+1]$^+$=1027 (Mw=1026 difunctional fragment); m/z [M+1]$^+$=662 (Mw=661 monofunctional fragment).

EXAMPLE 5

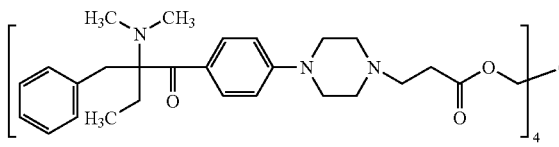

0.3616 g pentaerythritol tetraacrylate (mol. wt. 352) (0.00103 moles), 1.5 g of the product of Example 1 (0.00411 moles), toluene 10 ml and 0.05 g 1,8-diazabicyclo-(5.4.0) undec-7-ene (DBU) (catalyst) were mixed in a round bottomed flask equipped with a stirrer, condenser and temperature probe. The mixture was heated to reflux for a total of 6 hours. The mixture was then cooled and filtered, and then the solvent was removed on the rotary evaporator to yield the product.

Product yield 1.80 g viscous yellow/orange paste.

IR: acrylate C=C at 81 0 cm$^{-1}$ not present, indicating product has formed.

MS: m/z [M+1]$^+$=1083 (Mw=1082 difunctional fragment); m/z [M+1]$^+$=718 (Mw=717 monofunctional fragment).

EXAMPLE 6

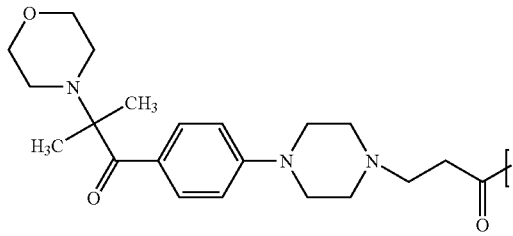

0.41 g PEG200 diacrylate (mol. wt. ~258, n=3 average) (0.00159 moles), 1.0 g of the product of Example 2 (0.00315 moles), toluene 10 ml and 0.04 g 1,8-diazabicyclo-(5.4.0) undec-7-ene (DBU) (catalyst) were mixed in a round bottomed flask equipped with a stirrer, condenser and temperature probe. The mixture was heated to reflux for a total of 6 hours. The mixture was then cooled and filtered, and then the solvent was removed on the rotary evaporator to yield the product.

Product yield 1.2 g of a viscous yellow/orange paste.

IR: acrylate C=C at 810 cm$^{-1}$ not present, indicating product has formed.

MS: m/z [M+1]$^+$=893 (Mw=892 difunctional product); m/z [M+1]$^+$=576 (Mw=575 monofunctional fragment).

EXAMPLE 7

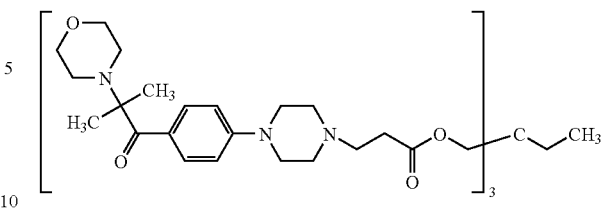

0.3112 g trimethylolpropane triacrylate (TMPTA, mol. wt. 296) (0.00105 moles), 1.0 g of the product of Example 2 (0.00315 moles), toluene 10 ml and 0.04 g 1,8-diazabicyclo (5.4.0)undec-7-ene (DBU) (catalyst) were mixed in a round bottomed flask equipped with a stirrer, condenser and temperature probe. The mixture was heated to reflux for a total of 6 hours. The mixture was then cooled and filtered, and then the solvent was removed on a rotary evaporator to yield the product.

Product yield 1.15 g of a viscous yellow/orange paste.

IR: acrylate C=C at 810 cm−1 not present, indicating product has formed.

MS: m/z [M+1]$^+$=931 (Mw=930 difunctional fragment); m/z [M+1]$^+$=614 (Mw=613 monofunctional fragment).

EXAMPLE 8

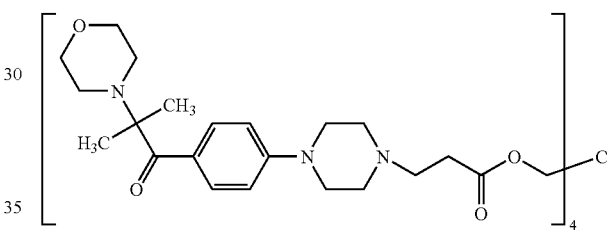

0.28 g pentaerythritol tetraacrylate (mol. wt. 352) (0.0008 moles), 1.0 g of the product of Example 1 (0.00315 moles), toluene 10 ml and 0.04 g 1,8-diazabicyclo-(5.4.0)undec-7-ene (DBU) (catalyst) were mixed in a round bottomed flask equipped with a stirrer, condenser and temperature probe. The mixture was heated to reflux for a total of 6 hours. The mixture was then cooled and filtered, and then the solvent was removed on a rotary evaporator to yield the product.

Product yield 1.2 g of a viscous yellow/orange paste.

IR: acrylate C=C at 810 cm$^{-1}$ not present, indicating product has formed.

MS: m/z [M+1]$^+$=987 (Mw=986 difunctional fragment); m/z [M+1]$^+$=670 (Mw=669 monofunctional fragment).

EXAMPLE 9

Performance Evaluation in Offset Inks

The performance of the new materials was assessed in a black offset ink formulation based on a tri-functional urethane acrylate oligomer. A photoinitiator blend was added as 8% of the overall formulation. The photoinitiator blend comprised methyl o-benzoylbenzoate (MBB), isopropylthioxanthone (ITX), 2-ethylhexyl p-dimethyl-aminobenzoate (EHA) and a multi-functional photoinitiator (MFPI), as prepared in one of the preceding Examples. The MFPI was used at a level of 13.5 weight % in the photoinitiator blend.

In the control formulation, the new MFPI was substituted by Irgacure 369 when comparing against the products from Examples 3, 4 and 5, or by Irgacure 907 when comparing against the products from Examples 6, 7 and 8, as would be typical in a normal commercial formulation.

A comparative formulation was also prepared that only comprised methyl o-benzoyl benzoate (MBB), isopropylthioxanthone (ITX) and 2-ethylhexyl p-dimethyl-aminobenzoate (EHA).

The inks were printed onto a carton board substrate (Incada Silk 260 gsm from Iggesund) to a density of approximately 1.8 using an IGT C1 print proofer. These were cured at 100 m/min using a Primarc Maxicure UV rig fitted with a single 300 W/inch medium pressure mercury lamp, operating at full power to provide good comparison of results. Cure was assessed using a Specac set off blocking test at 10 tons pressure for 5 seconds at each pass. The number of passes to achieve no set off of partially cured ink onto apiece of blank substrate was recorded and is shown in Table 1.

TABLE 1

Cure speed of inks

| Initiator | No. of passes to cure |
|---|---|
| Irgacure 369 | 2 |
| Example 3 | 3 |
| Example 4 | 3 |
| Example 5 | 3 |
| Irgacure 907 | 2 |
| Example 6 | 2 |
| Example 7 | 2-3 |
| Example 8 | 2-3 |
| Comparative formulation | 4-5 |

The results in Table 1 show that the new MFPI materials give good cure speed. In the case of Example 6, the cure speed is as good as the standard formulations. In the case of Examples 3, 4, 5, 7 and 8, the cure speed is almost as good as the standard formulations. In all cases the cure speed is better than the comparative formulation.

It should be noted that the results outlined above have been obtained from a direct weight % replacement of the standard photoinitiator by the new materials in the formulation.

Overall, the results show that these novel materials have good photoinitiator activity. These new compounds also have the potential to achieve low levels of photolysis product migration and low odour from the cured print due to the initiator moieties being bound to a high molecular weight core. When these two factors are combined these new materials have considerable advantages over the existing technology.

EXAMPLE 10

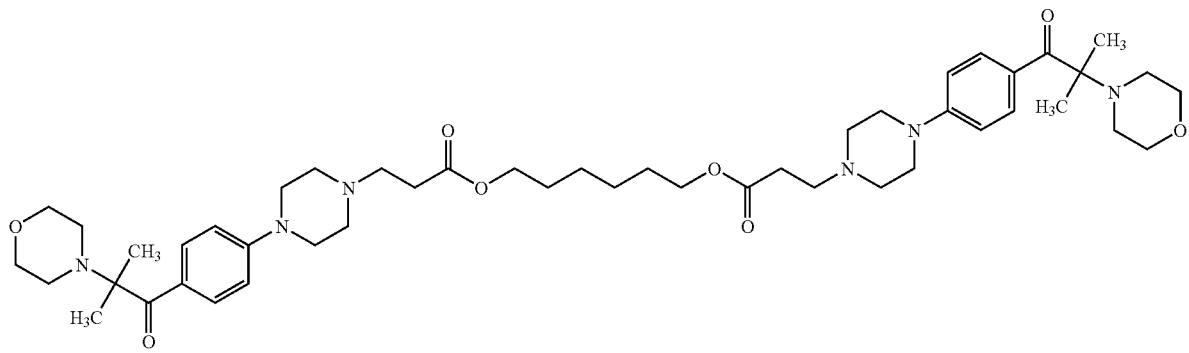

3.5 g hexanediol diacrylate (0.0155 moles), 11.08 g of the product of Example 2 (0.0349 moles), toluene 30 ml and 0.35 g 1,8-diazabicyclo(5.4.0)undec-7-ene (DBU) (catalyst) were mixed in a round bottomed flask equipped with a stirrer, condenser and temperature probe. The mixture was heated to reflux for a total of 10 hours. The mixture was then cooled and filtered, and then the solvent was removed on a rotary evaporator to yield the product.

Product yield 14.10 g of a viscous yellow/orange paste.

IR: acrylate C=C at 810 cm$^{-1}$ not present indicating product has formed.

MS: m/z [M+1]$^+$=862 (Mw=861 difunctional product); m/z [M+1]$^+$=544 (Mw=543 monofunctional fragment).

EXAMPLE 11

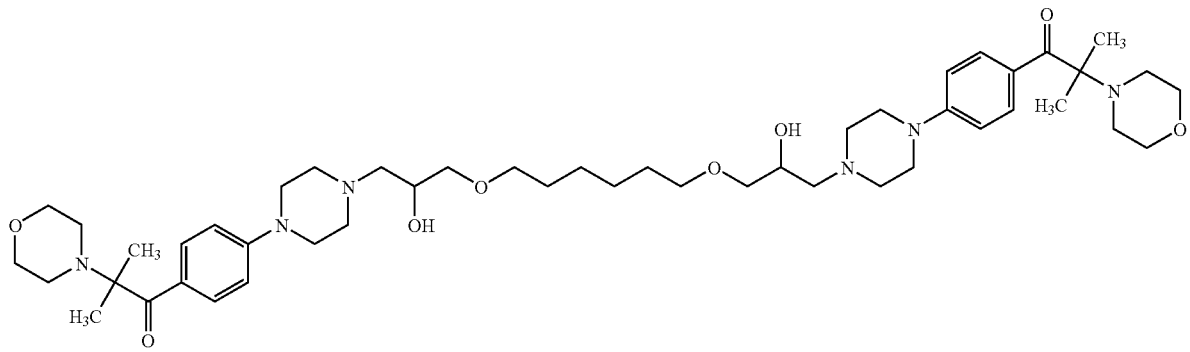

3.5 g hexanediol diglycidyl ether (0.0152 moles), 9.663 g of the product of Example 2 (0.0304 moles), and toluene 30 ml were mixed in a round bottomed flask equipped with a stirrer, condenser and temperature probe. The mixture was heated to reflux for a total of 10 hours. The mixture was then cooled and filtered, and then the solvent was removed on a rotary evaporator to yield the product.

Product yield 12.61 g of a viscous yellow/orange paste.

IR: no peak due to glycidyl indicating product has formed.

MS: m/z [M+1]$^+$=866 (Mw=865 difunctional product); m/z [M+1]$^+$=548 (Mw=547 monofunctional fragment).

EXAMPLE 12

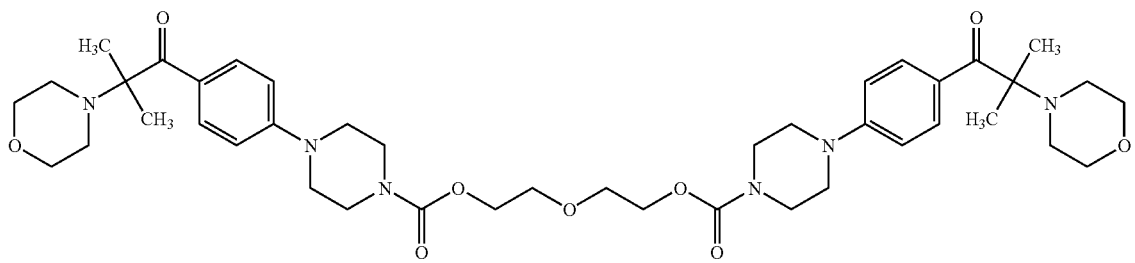

10.0 g of the product of Example 2 (0.0317 moles), 3.18 g of triethylamine (0.0316 moles) and 50 ml of toluene were mixed in a two necked flask equipped with a stirrer, condenser and a temperature probe. 3.39 g of diethylene glycol bischloroformate (0.01575 moles) in 20 ml of toluene were then added slowly, ensuring the exotherm was controlled (temperature maximum throughout the addition was 33° C). After the addition was complete, the mixture was stirred for 2 hours, allowing the mixture to cool to room temperature. The mixture was then filtered to remove the insoluble triethylamine hydrochloride formed during the reaction. The toluene was then removed on a rotary evaporator to yield the product.

Product yield 12.5 g of a viscous yellow paste.

The product was analysed by IR and LCMS.

IR: peak at 1704 cm$^{-1}$ due to product.

MS: m/z [M+1]$^+$=794 (Mw=793 difunctional product).

EXAMPLE 13

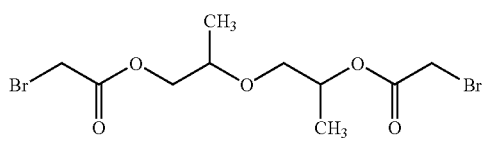

22.78 g 2-Bromoacetic acid (0.164 moles) and 10.0 g dipropylene glycol (0.7453 moles) were azeotropically refluxed for 5 hours in 60 ml toluene using 0.33 g p-toluenesulphonic acid as a catalyst and 0.07 g butylated hydroxytoluene as a stabiliser. The solution was then cooled and washed twice with 100 ml 10% aqueous potassium carbonate solution and twice with 100 ml deionised water before azeotroping to dryness and removing all solvent on a rotary evaporator to yield a colourless low viscosity liquid.

Product yield=27.0 g

The product was analysed by IR.

IR: Strong peak due to ester at 1736 cm$^{-1}$.

EXAMPLE 14

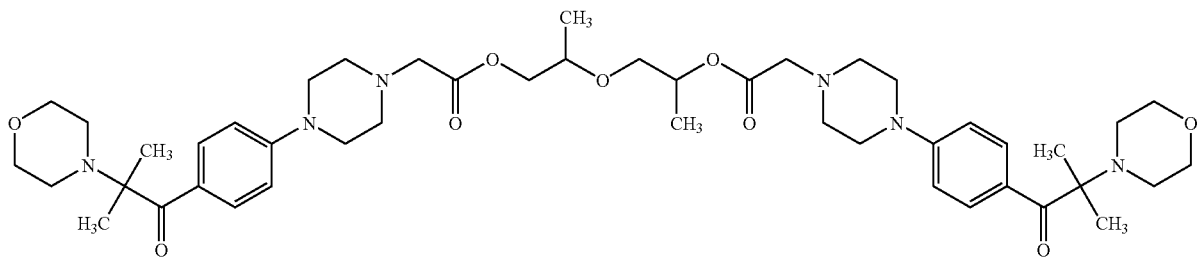

10.0 g of the product of Example 2 (0.317 moles), 3.18 g of triethylamine (0.315 moles) and 50 ml of toluene were mixed in a round bottomed flask equipped with a stirrer, condenser and temperature probe. 5.64 g of the product of Example 13 were added slowly ensuring the exotherm was controlled. The mixture was then heated to reflux for a total of 10 hours. The mixture was then filtered to remove the insoluble residue, and the solvent was then removed by a rotary evaporator to yield the product.

Product yield=12.6 g

The product was analysed by IR and LCMS.

IR: Strong peak due to ester at 1747 $cm^{-1}$.

MS: m/z $[M+1]^+$=850 (Mw=849 difunctional product).

EXAMPLE 15

Performance Evaluation in Offset Inks

The performance of the new materials was assessed in a black offset ink formulation based on a tri-functional urethane acrylate oligomer. A photoinitiator blend was added as 8% of the overall formulation. The photoinitiator blend comprised methyl o-benzoylbenzoate (MBB), isopropylthioxanthone (ITX), 2-ethylhexyl p-dimethylaminobenzoate (EHA) and the new Multi-functional photoinitiator (MFPI). The new MFPI was used at a level of 15 weight % in the photoinitiator blend.

In the control formulation, the new MFPI were substituted by Irgacure 369, as would typically be used in commercial formulations.

A comparative formulation was also prepared that only comprised methyl o-benzoylbenzoate (MBB), isopropylthioxanthone (ITX) and 2-ethylhexyl p-dimethylaminobenzoate (EHA) with no aminoalkylphenone present. In this case the ratio of these 3 components is still the same as that used in the test formulations.

The inks were printed onto a carton board substrate (Incada Silk 260 gsm from Iggesund) to a density of approximately 1.8 using an IGT C1 print proofer. These were cured at 100 m/min using a Primarc Maxicure UV rig fitted with a single 300 W/inch medium pressure mercury lamp, operating at half power to provide good comparison of results. Cure is assessed using a Specac set off blocking test at 10 tons pressure for 5 seconds at each pass. The results are shown in Table 2.

TABLE 2

Cure speed of inks containing new MFPI derivatives

| Initiator | No. of passes to cure |
| --- | --- |
| No aminoalkyl phenone | 5 |
| Irgacure 369 | 3 |

TABLE 2-continued

Cure speed of inks containing new MFPI derivatives

| Initiator | No. of passes to cure |
| --- | --- |
| Example 3 | 3 |
| Example 10 | 3 |
| Example 11 | 3 |
| Example 12 | 3 |
| Example 14 | 3-4 |

The results in Table 2 show that the new MFPI materials give enhanced cure speed, with performance comparable to that of the well known highly reactive aminoalkyl phenone Irgacure 369. In all cases the cure speed is significantly better than the comparative formulation containing no aminoalkyl phenone.

It should be noted that the results outlined above have been obtained from a direct weight % replacement of the standard photoinitiator by the new materials in the formulation.

Overall, the results show that these novel materials have good photoinitiator activity. This new technology also has the potential to achieve low levels of photolysis product migration and low odour from the cured print due to the initiator moieties being bound to a high molecular weight core. When these two factors are combined these new materials have considerable advantages over the existing technology.

The invention claimed is:

1. A compound of formula (I):

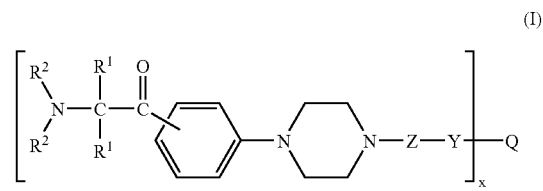

where:
the substituents $R^1$ are individually selected from $C_1$-$C_{10}$ alkyl groups and optionally substituted benzyl groups;
the substituents $R^2$ are individually selected from alkyl groups or, together with the nitrogen atom to which they are attached, represent a nitrogen-containing heterocyclic group;
Z is selected from $C_6$-$C_{10}$ arylene groups and groups of formula —$(CHR^3)_n$—,
where $R^3$ is a hydrogen atom, a hydroxy group or a $C_1$-$C_4$ alkyl group, and n is a number from 0 to 6;

Y is selected from carbonyl groups and the —$CH_2$— group;

Q is selected from the residues of mono- or poly-hydroxy compounds having from 1 to 6 hydroxy groups; and x is a number from 1 to 6;

and esters thereof.

2. A compound according to claim 1, where at least one of the $R^1$ substituents is a $C_1$-$C_6$ alkyl group.

3. A compound according to claim 2, where at least one of the $R^1$ substituents is a methyl or ethyl group.

4. A compound according to claim 2, where at least one of the $R^1$ substituents is a benzyl group.

5. A compound according to claim 1, where the substituents $R^2$ are individually selected from $C_1$-$C_6$ alkyl groups.

6. A compound according to claim 5, where the $R^2$ substituent represents a methyl or ethyl group.

7. A compound according to claim 1, where the $R^2$ substituents, together with the nitrogen atom to which they are attached, represent a 5- to 7-membered nitrogen-containing heterocyclic ring.

8. A compound according to claim 7, where nitrogen-containing said heterocyclic ring is selected from morpholino, piperidino, 1-pyrrolidinyl, 3-alkyl-1-imidazolidinyl, 2-alkyl-1-pyrazolidinyl, 4-alkyl-1-piperazinyl, 1-pyrrolyl, 1-imidazolyl and 1-pyridyl groups.

9. A compound according to claim 8, where said heterocyclic ring is selected from piperidino, morpholino and 4-methyl-1-piperazinyl groups.

10. A compound according to claim 1, where Z is a group of formula —$(CHR^3)_n$—, and n is 1 or 2.

11. A compound according to claim 1, where Z is a group of formula —$(CHR^3)_n$—, and n is 2.

12. A compound according to claim 10, where $R^3$ is selected from hydrogen atoms, methyl groups and ethyl groups.

13. A compound according to claim 12, where $R^3$ is a hydrogen atom.

14. A compound according to claim 1, where Z is a group of formula —$(CHR^3)_n$—, n is a number from 2 to 6 and one $R^3$ represents a hydrogen atom or a $C_1$-$C_4$ alkyl group, and the other or others of $R^3$ represent hydrogen atoms.

15. A compound according to claim 1, where Z is a phenylene group.

16. A compound according to claim 1, wherein Q is a group of formula -$A_x$-Q', where:

A is selected from groups of formula —[O(CHR$^4$CHR$^5$)$_a$]$_y$—, —[O(CH$_2$)$_b$CO]$_y$— and —[O(CH$_2$)$_b$CO]$_{(y-1)}$—[O(CHR$^4$CHR$^5$)$_a$]— where:

$R^4$ and $R^5$ are individually selected from hydrogen atoms and $C_1$-$C_4$ alkyl groups;

a is a number from 1 to 2;

b is a number from 4 to 5; and y is a number from 1 to 10;

x is a number from 1 to 6; and

Q' is selected from residues of a mono- or poly-hydroxy compounds having from 1 to 6 hydroxy groups.

17. A compound according to claim 16, where y is a number from 3 to 10.

18. A compound according to claim 17, where A is a group of formula —[O(CHR$^4$CHR$^5$)$_a$]$_y$— where a is an integer from 1 to 2, and y is a number from 1 to 10.

19. A compound according to claim 17, where A is selected from groups of formula —[OCH$_2$CH$_2$]$_y$—, —[OCH$_2$CH$_2$CH$_2$CH$_2$]$_y$— and —[OCH(CH$_3$)CH$_2$]$_y$—, where y is a number from 1 to 10.

20. A compound according to claim 17, where A is a group of formula —[O(CH$_2$)$_b$CO]$_y$—, where b is a number from 4 to 5 and y is a number from 1 to 10.

21. A compound according to claim 17, where A is a group of formula —[O(CH$_2$)$_b$CO]$_{(y-1)}$—[O(CHR$^4$CHR$^5$)$_a$]—, where a is a number from 1 to 2, b is a number from 4 to 5 and y is a number from 1 to 10.

22. A compound according to claim 16, where x is 2.

23. A compound according to claim 16, where y is a number from 1 to 6.

24. A compound according to claim 16, where the residue -$A_x$-Q' has a molecular weight no greater than 2000.

25. A compound according to claim 24, where the residue -$A_x$-Q' has a molecular weight no greater than 1200.

26. A compound according to claim 25, where the residue -$A_x$-Q' has a molecular weight no greater than 1000.

27. A compound according to claim 26, where the residue -$A_x$-Q' has a molecular weight no greater than 800.

28. A compound according to claim 16, where Q' is a residue of a poly($C_2$-$C_6$ alkylene)glycol.

29. A compound according to claim 16, where Q' is a residue of ethylene glycol, propylene glycol, butylene glycol, glycerol, 2,2-propanediol, polyethylene glycol, polypropylene glycol, polybutylene glycol, trimethylolpropane, di-trimethylolpropane, pentaerythritol or di-pentaerythritol.

30. A compound according to claim 1, where x is 1.

31. A compound according to claim 30, where Q is the residue of a compound of formula $R^6$—OH, where $R^6$ is selected from $C_1$-$C_{10}$ alkyl groups and optionally substituted benzyl groups.

32. A compound according to claim 30, where Q is a $C_1$-$C_6$ alkoxy group or a phenoxy group.

33. A compound according to claim 31, where Z is a phenylene group.

34. A compound according to claim 1, where Q is a residue of a poly($C_2$-$C_6$ alkylene)glycol.

35. A compound according to claim 34, where Q is a residue of ethylene glycol, propylene glycol, butylene glycol, glycerol, 2,2-propanediol, polyethylene glycol, polypropylene glycol, polybutylene glycol, trimethylolpropane, di-trimethylolpropane, pentaerythritol or di-pentaerythritol.

36. An energy-curable composition comprising: (a) a polymerisable monomer, prepolymer or oligomer; and (b) a compound as claimed in claim 1 as photoinitiator.

37. A process for preparing an energy cured polymeric composition comprising a step of exposing a composition according to claim 36 to radiant energy.

38. A process according to claim 37, where the radiant energy is ultraviolet radiation.

* * * * *